United States Patent
Collier et al.

(10) Patent No.: US 7,659,283 B2
(45) Date of Patent: Feb. 9, 2010

(54) PYRROLO [3,2-C] PYRIDINES USEFUL AS INHIBITORS OF PROTEIN KINASES

(75) Inventors: Philip Noel Collier, Abingdon (GB); Juan-Miguel Jimenez, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 137 days.

(21) Appl. No.: 11/705,556

(22) Filed: Feb. 12, 2007

(65) Prior Publication Data
US 2007/0213327 A1    Sep. 13, 2007

Related U.S. Application Data

(60) Provisional application No. 60/773,143, filed on Feb. 14, 2006.

(51) Int. Cl.
*A01N 43/42*    (2006.01)
*A61K 31/44*    (2006.01)
*C07D 471/02*    (2006.01)
*C07D 491/02*    (2006.01)

(52) U.S. Cl. ....................... 514/300; 546/113
(58) Field of Classification Search ............... 546/113; 524/300
See application file for complete search history.

(56) References Cited

U.S. PATENT DOCUMENTS

| | | | |
|---|---|---|---|
| 6,369,227 B1* | 4/2002 | Lam et al. | 546/113 |
| 2005/0239820 A1* | 10/2005 | Borzilleri et al. | 514/300 |

FOREIGN PATENT DOCUMENTS

| | | |
|---|---|---|
| WO | WO 99/20624 A1 | 4/1999 |
| WO | WO 00/39108 A1 | 7/2000 |
| WO | WO 2006/114180 A1 | 11/2006 |

OTHER PUBLICATIONS

Park et al., Immunology, (Sep. 2005) vol. 116, No. 1, pp. 71-81.*
International Search Report received in the corresponding PCT Application No. PCT/US2007/003767.

* cited by examiner

*Primary Examiner*—D. Margaret Seaman
*Assistant Examiner*—Niloofar Rahmani
(74) *Attorney, Agent, or Firm*—Booyoong S. Lim; Lisa A. Dixon; Vertex Pharmaceuticals Incorporated

(57) ABSTRACT

The present invention relates to compounds useful as inhibitors of protein kinase. The invention also provides pharmaceutically acceptable compositions comprising said compounds and methods of using the compositions in the treatment of various disease, conditions, or disorders. The invention also provides processes for preparing compounds of the inventions.

38 Claims, No Drawings

PYRROLO [3,2-C] PYRIDINES USEFUL AS INHIBITORS OF PROTEIN KINASES

CROSS REFERENCE TO RELATED APPLICATIONS

This application claims priority to U.S. Provisional Patent Application 60/773,143, filed Feb. 14, 2006, the content of which is incorporated by reference.

TECHNICAL FIELD OF THE INVENTION

The present invention relates to compounds useful as inhibitors of protein kinases. The invention also relates to pharmaceutically acceptable compositions comprising the compounds of the invention and methods of using the compositions in the treatment of various disorders. The invention also relates to processes for preparing the compounds of the invention.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S., The Protein Kinase Facts Book, I and II, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., FASEB J. 1995, 9, 576-596; Knighton et al., Science 1991, 253, 407-414; Hiles et al., Cell 1992, 70, 419-429; Kunz et al., Cell 1993, 73, 585-596; Garcia-Bustos et al., EMBO J. 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor a (TNF-a)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

One kinase family of particular interest is the Src family of kinases. These kinases are implicated in cancer, immune system dysfunction and bone remodeling diseases. For general reviews, see Thomas and Brugge, Annu. Rev. Cell Dev. Biol. 1997, 13, 513; Lawrence and Niu, Pharmacol. Ther. 1998, 77, 81; Tatosyan and Mizenina, Biochemistry (Moscow) 2000, 65, 49-58; Boschelli et al., Drugs of the Future 2000, 25(7), 717.

Members of the Src family include the following eight kinases in mammals: Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. Biochemistry (Moscow) 2000, 65, 49-58.

Based on published studies, Src kinases are considered as potential therapeutic targets for various human diseases. Mice that are deficient in Src develop osteoporosis, or bone build-up, because of depressed bone resorption by osteoclasts. This suggests that osteoporosis resulting from abnormally high bone resorption can be treated by inhibiting Src. Soriano et al., Cell 1992, 69, 551 and Soriano et al., Cell 1991, 64, 693.

Suppression of arthritic bone destruction has been achieved by the overexpression of CSK in rheumatoid synoviocytes and osteoclasts. Takayanagi et al., J. Clin. Invest. 1999, 104, 137. CSK, or C-terminal Src kinase, phosphorylates and thereby inhibits Src catalytic activity. This implies that Src inhibition may prevent joint destruction that is characteristic in patients suffering from rheumatoid arthritis. Boschelli et al., Drugs of the Future 2000, 25(7), 717.

Src also plays a role in the replication of hepatitis B virus. The virally encoded transcription factor HBx activates Src in a step required for propagation of the virus. Klein et al., EMBO J. 1999, 18, 5019, and Klein et al., Mol. Cell. Biol. 1997, 17, 6427.

A number of studies have linked Src expression to cancers such as colon, breast, hepatic and pancreatic cancer, certain B-cell leukemias and lymphomas. Talamonti et al., J. Clin. Invest. 1993, 91, 53; Lutz et al., Biochem. Biophys. Res. 1998 243, 503; Rosen et al., J. Biol. Chem. 1986, 261, 13754; Bolen et al., Proc. Natl. Acad. Sci. USA 1987, 84, 2251; Masaki et al., Hepatology 1998, 27, 1257; Biscardi et al., Adv. Cancer Res. 1999, 76, 61; Lynch et al., Leukemia 1993, 7, 1416. Furthermore, antisense Src expressed in ovarian and colon tumor cells has been shown to inhibit tumor growth. Wiener et al., Clin. Cancer Res., 1999, 5, 2164; Staley et al., Cell Growth Diff. 1997, 8, 269.

Other Src family kinases are also potential therapeutic targets. Lck plays a role in T-cell signaling. Mice that lack the Lck gene have a poor ability to develop thymocytes. T-cells lacking Lck are shown to be severely impaired in TCR tyrosine phosphorylation and subsequent activation via the TCR. Straus et al., Cell 1992, 70, 585; Chan et al., Ann. Rev. Immunol. 1994, 12, 555; Weiss et al., Cell 1994, 76, 263; Hanke et al., J. Biol. Chem. 1996, 271, 695; Van Oers at al., Immunity 1996, 5, 429. The function of Lck as a positive activator of T-cell signaling suggests that Lck inhibitors may be useful for treating of T cell mediated disorders such as autoimmune and inflammatory diseases and in the prevention of solid organ transplant rejection. Molina et al., Nature, 1992, 357, 161; Hanke et al., Inflammation Res. 1995, 44, 357. Hck, Fgr and Lyn have been identified as important mediators of integrin signaling in myeloid leukocytes. Lowell et al., J. Leukoc. Biol., 1999, 65, 313. Inhibition of these kinase mediators may therefore be useful for treating inflammation. Boschelli et al., Drugs of the Future 2000, 25(7), 717.

There is therefore a need for inhibitors of Src family protein kinases.

SUMMARY OF THE INVENTION

Compounds of this invention, and pharmaceutically acceptable compositions thereof, are useful as inhibitors of protein kinases. In some embodiments, these compounds are useful as inhibitors of Src family protein kinases; in some embodiments, as inhibitors of Lck protein kinases. These compounds have the formula I, as defined herein, or a pharmaceutically acceptable salt thereof.

These compounds and pharmaceutically acceptable compositions thereof are useful for treating or preventing a variety of diseases, disorders or conditions, including, but not limited to, an autoimmune, inflammatory, proliferative, or hyperproliferative disease, an immunologically-mediated disease, or bone disease. The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

This invention provides compounds of Formula I:

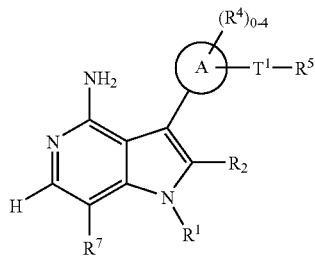

I wherein:
$R^1$ is $C_{1-6}$haloalkyl, Q, or -Z-Q;
$R^2$ is H, halo, CN, $NO_2$, $C_{1-4}$haloaliphatic, $C_{3-6}$cycloaliphatic, or $C_{1-6}$aliphatic;
Ring A is a 3-8-membered saturated, partially unsaturated, or fully unsaturated monocyclic ring having 0-3 heteroatoms independently selected from O, N, and S; or an 8-12 membered saturated, partially unsaturated, or fully unsaturated bicyclic ring having 0-5 heteroatoms independently selected from O, N, and S;
$R^4$ is H, $C_{1-6}$aliphatic, $C_{3-6}$cycloaliphatic, or —$(Y)_n$—$V^1$;
wherein
n is 0 or 1;
Y is unsubstituted $C_{1-6}$aliphatic optionally replaced with 0-3 occurrences of —NR—, —O—, —S—, —C(O)—, —SO—, or —$SO_2$—;
$V^1$ is $C_{3-6}$cycloaliphatic, halo($C_{1-4}$ aliphatic), 3-6 membered heterocyclyl, halo, $NO_2$, CN, OH, OR", SH, SR", $NH_2$, NHR", N(R")$_2$, COH, COR", $CO_2H$, $CO_2R$", $CONH_2$, CONHR", CONR"$_2$, OCOR", OCONH$_2$, OCONHR", OCON(R")$_2$, NHCOR", NR"COR", $NHCO_2R$", $NR"CO_2R$", $NHCO_2H$, $NR"CO_2H$, NHCONH$_2$, NHCONHR", NHCON(R")$_2$, $SO_2NH_2$, $SO_2NHR$", $SO_2N(R")_2$, $NHSO_2R$", or $NR"SO_2R$";
R" is unsubstituted $C_{1-4}$ aliphatic;
$T^1$ is $C_{1-6}$aliphatic optionally replaced with 0-3 occurrences of —NR—, —O—, —S—, —C(O)—, —C(=NR)—, —C(=NOR)—, —SO—, or —$SO_2$—; each $T^1$ is optionally substituted with 0-2 $J^T$;
$R^5$ is H; $C_{1-6}$aliphatic optionally replaced with 0-2 occurrences of O, N, and S; 3-8-membered saturated, partially unsaturated, or fully unsaturated monocyclic ring having 0-3 heteroatoms independently selected from O, N, and S; or an 8-12 membered saturated, partially unsaturated, or fully unsaturated bicyclic ring having 0-5 heteroatoms independently selected from O, N, and S; each $R^5$ is optionally substituted with 0-5 $J^5$;
$R^7$ is H or halo;
Z is $C_{1-6}$aliphatic optionally replaced with 0-3 occurrences of —NR—, —O—, —S—, —C(O)—, —C(S)—, —C(=NR)—, —C(=NOR)—, —SO—, or —$SO_2$—; each Z is optionally substituted with 0-2 $J^Z$;
Q is H; $C_{1-6}$ aliphatic; a 3-8-membered saturated, partially unsaturated, or fully unsaturated monocyclic ring having 0-3 heteroatoms independently selected from O, N, and S; or an 8-12 membered saturated, partially unsaturated, or fully unsaturated bicyclic ring having 0-5 heteroatoms independently selected from O, N, and S; each Q is optionally substituted with 0-5 $J^Q$;
each $J^Z$ is independently H, halo, $C_{1-6}$ aliphatic, $C_{3-6}$cycloaliphatic, $NO_2$, CN, —$NH_2$, —NH($C_{1-4}$ aliphatic), —N($C_{1-4}$ aliphatic)$_2$, —OH, —O($C_{1-4}$ aliphatic), —$CO_2H$, —$CO_2$($C_{1-4}$ aliphatic), —O(halo$C_{1-4}$ aliphatic), or halo($C_{1-4}$ aliphatic);
$J^5$ is M or —Y-M;
each Y is independently an unsubstituted $C_{1-6}$aliphatic optionally replaced with 0-3 occurrences of —NR—, —O—, —S—, —C(O)—, —SO—, or —$SO_2$—;
each M is independently H, $C_{1-6}$ aliphatic, $C_{3-8}$cycloaliphatic, halo($C_{1-4}$ aliphatic), —O(halo$C_{1-4}$ aliphatic), 3-8 membered heterocyclyl, halo, $NO_2$, CN, OH, OR', SH, SR', $NH_2$, NHR', N(R')$_2$, COH, COR', $CO_2H$, $CO_2R$', $CONH_2$, CONHR', CONR'$_2$, OCOR', OCONH$_2$, OCONHR', OCON(R')$_2$, NHCOR', NR'COR', $NHCO_2R$', $NR'CO_2R$', $NHCO_2H$, $NR'CO_2H$, NHCONH$_2$, NHCONHR', NHCON(R')$_2$, $SO_2NH_2$, $SO_2NHR$', $SO_2N(R')_2$, $NHSO_2R$', $NR'SO_2R$', POR', $PO_2R$', PO(R')$_2$, or PO(OR')$_2$;
$J^Q$ is $M^1$ or —$Y^1$-$M^1$;
each $Y^1$ is independently an unsubstituted $C_{1-6}$aliphatic optionally replaced with 0-3 occurrences of —NR—, —O—, —S—, —C(O)—, —SO—, or —$SO_2$—;
each $M^1$ is independently H, $C_{1-6}$ aliphatic, $C_{3-8}$cycloaliphatic, halo($C_{1-4}$ aliphatic), —O(halo$C_{1-4}$ aliphatic), 3-8 membered heterocyclyl, 5-6 membered heteroaryl, phenyl, halo, $NO_2$, CN, OH, OR', SH, SR', $NH_2$, NHR', N(R')$_2$, COH, COR', $CO_2H$, $CO_2R$', $CONH_2$, CONHR', CONR'$_2$, OCOR', OCONH$_2$, OCONHR', OCON(R')$_2$, NHCOR', NR'COR', $NHCO_2R$', $NR'CO_2R$', $NHCO_2H$, $NR'CO_2H$, NHCONH$_2$, NHCONHR', NHCON(R')$_2$, $SO_2NH_2$, $SO_2NHR$', $SO_2N(R')_2$, $NHSO_2R$', $NR'SO_2R$', POR', $PO_2R$', PO(R')$_2$, or PO(OR')$_2$;
each M and $M^1$ is independently and optionally substituted with 0-5 $J^M$;
R is H or unsubstituted $C_{1-6}$aliphatic;
R' is unsubstituted $C_{1-6}$aliphatic; or two R' groups, together with the atom to which they are bound, form an unsubstituted 3-8 membered nonaromatic monocyclic ring having 0-1 heteroatoms independently selected from O, N, and S; each $J^T$ and $J^M$ is independently H, halo, $C_{1-6}$ aliphatic, $C_{3-6}$cycloaliphatic, $NO_2$, CN, $—NH_2$, $—NH(C_{1-4}$ aliphatic), $—N(C_{1-4}$ aliphatic)$_2$, $—OH$, $—O(C_{1-4}$ aliphatic), COH, $—CO(C_{1-4}$ aliphatic), $CONH_2$, $CONH(C_{1-4}$ aliphatic), $CON(C_{1-4}$ aliphatic)$_2$, $—CO_2H$, $—CO_2(C_{1-4}$ aliphatic), $—O(haloC_{1-4}$ aliphatic), or halo($C_{1-4}$ aliphatic).

In some embodiments,

Ring A is not

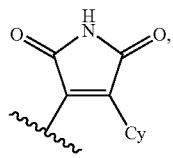

wherein Cy is any cyclic moiety;

when Q is an optionally substituted 5-membered saturated ring with 1-3 heteroatoms selected from O and S; then $J^Q$ is not $—(CH_2)_q—PO(OR)_2$, wherein
q is 0 or 1 and
R is H or unsubstituted $C_{1-6}$aliphatic;

when $R^1$ and $R^2$ are both H, then ring A is not

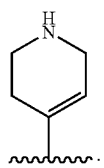

These compounds, and pharmaceutically acceptable compositions thereof, are useful for treating or lessening the severity of a variety of disorders including hypercalcemia, osteoporosis, osteoarthritis, cancer, symptomatic treatment of bone metastasis, Paget's disease, autoimmune diseases such as transplant rejection, allergies, rheumatoid arthritis, and leukemia.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "cycloaliphatic" (or "carbocycle" or "carbocyclyl" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g., cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Exemplary protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, an alkyl or aliphatic chain can be optionally replaced with another atom or group. This means that a methylene unit of the alkyl or aliphatic chain is optionally replaced with said other atom or group. Examples of such atoms or groups would include, but are not limited to, —NR—, —O—, —C(O)—, —C(=N—CN)—, —C(=NR)—, —C(=NOR)—, —S—, —SO—, or —SO$_2$—. These atoms or groups can be combined to form larger groups. Examples of such groups include, but are not limited to, —OC(O)—, —C(O)CO—, —CO$_2$—, —C(O)NR—, —C(=N—CN), —NRCO—, —NRC(O)O—, —SO$_2$NR—, —NRSO$_2$—, —NRC(O)NR—, —OC(O)NR—, and —NRSO$_2$NR—, wherein R is defined herein.

Unless otherwise specified, the optional replacements form a chemically stable compound. Optional replacements can occur both within the chain and at either end of the chain; i.e., both at the point of attachment and/or also at the terminal end. Two optional replacements can also be adjacent to each other within a chain so long as it results in a chemically stable compound.

The optional replacements can also completely replace all of the carbon atoms in a chain. For example, a C$_3$ aliphatic can be optionally replaced by —NR—, —C(O)—, and —NR— to form —NRC(O)NR— (a urea).

Unless otherwise specified, if the replacement occurs at the terminal end, the replacement atom is bound to an H on the terminal end. For example, if —CH$_2$CH$_2$CH$_3$ were optionally replaced with —O—, the resulting compound could be —OCH$_2$CH$_3$, —CH$_2$OCH$_3$, or —CH$_2$CH$_2$OH.

Unless otherwise stated, structures depicted herein are also meant to include all isomeric (e.g., enantiomeric, diastereomeric, geometric, conformational, and rotational forms of the structure). For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

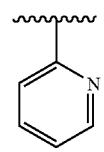

also represents

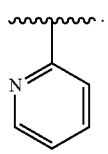

Therefore, single stereochemical isomers as well as enantiomeric, diastereomeric, geometric, conformational, or rotational mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

It will also be appreciated that certain of the compounds of present invention can exist in free form for treatment, or where appropriate, as a pharmaceutically acceptable salt.

As used herein, the term "pharmaceutically acceptable salt" refers to salts of a compound which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. This invention also envisions the quaternization of any basic nitrogen-containing groups of the compounds disclosed herein. Water or oil-soluble or dispersible products may be obtained by such quaternization.

Base addition salts can be prepared by 1) reacting the purified compound in its acid form with a suitable organic or inorganic base and 2) isolating the salt thus formed. Base addition salts include alkali or alkaline earth metal salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

The following abbreviations are used:
Pd(PPh$_3$)$_4$ tetrakis(triphenylphosphine)palladium(0)
dba dibenzylideneacetone
BINAP 2,2'-bis(diphenylphosphino)-1,1'-binaphthyl
TsCl para-toluenesulfonyl chloride
N,N-DMF N,N-dimethylformamide
EtOAc ethyl acetate
PE petroleum ether
DMSO dimethyl sulfoxide
TCA trichloroacetic acid
ATP adenosine triphosphate
Ac acetyl
Ph phenyl
Me methyl
NaOtBu Sodium tert-butoxide
HEPES 4-(2-hydroxyethyl)-1-piperazineethanesulfonic acid
BSA bovine serum albumin
DTT dithiothreitol
NMR nuclear magnetic resonance
HPLC high performance liquid chromatography
LCMS liquid chromatography-mass spectrometry
Rt retention time In some aspects of this invention, R$^2$ is H.

In other aspects, R$^1$ is Q.

In one aspect of this invention, Q is a 3-8-membered saturated, partially unsaturated, or fully unsaturated monocyclic ring having 0-3 heteroatoms independently selected from O, N, and S. In some embodiments, Q is a 3-8-membered saturated monocyclic ring having 0-3 heteroatoms independently selected from O, N, and S. In other embodiments, Q is a 3-8-membered saturated monocyclic ring having 0 heteroatoms. In some embodiments, Q is cyclohexyl or cyclopentyl.

In another aspect of this invention, J$^Q$ is a 3-8 membered heterocyclyl. In some embodiments, J$^Q$ is a 6-membered heterocyclyl containing 1-2 nitrogen atoms.

In one aspect of this invention, ring A is fully unsaturated (i.e., aromatic). In another aspect, ring A is partially unsaturated or saturated. In some embodiments, Ring A is a monocyclic ring. In other embodiments, Ring A is a bicyclic ring. In some embodiments, Ring A is a 5-membered ring. In other embodiments, Ring A is a 6-membered ring.

In some aspects of this invention, -T-R$^5$ is meta or para substituted. In other aspects, T is —C(O)NR— or —NRC(O)—.

In some embodiments, R is H.

According to one aspect of this invention, R$^5$ is a 3-8-membered saturated, partially unsaturated, or fully unsaturated monocyclic ring having 0-3 heteroatoms independently selected from O, N, and S; or an 8-12 membered saturated, partially unsaturated, or fully unsaturated bicyclic ring having 0-5 heteroatoms independently selected from O, N, and S. In some embodiments, R$^5$ is fully unsaturated (i.e., aromatic). In other embodiments, R$^5$ is partially unsaturated or saturated.

According to another aspect of this invention, R$^4$ is H, halo, C$_{1-6}$ aliphatic, C$_{3-6}$cycloaliphatic, NO$_2$, CN, —NH$_2$, —NH(C$_{1-4}$ aliphatic), —N(C$_{1-4}$ aliphatic)$_2$, —OH, —O(C$_{1-4}$ aliphatic), CONH$_2$, CONH(C$_{1-4}$ aliphatic), CON(C$_{1-4}$ aliphatic)$_2$, COH, —CO(C$_{1-4}$ aliphatic), —CO$_2$H, —CO$_2$(C$_{1-4}$ aliphatic), —O(haloC$_{1-4}$ aliphatic), or halo(C$_{1-4}$ aliphatic).

One embodiment provides the following compound:

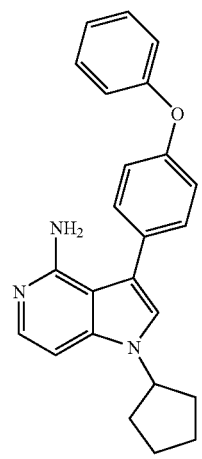

I-1

General Synthetic Methodology

The compounds of this invention may be prepared in general by methods such as those depicted in the general schemes below, and the preparative examples that follow.

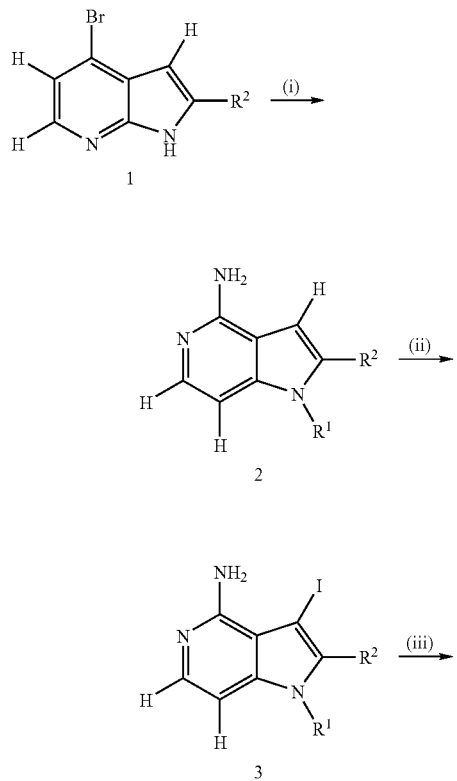

Scheme 1

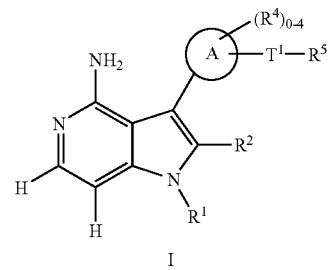

I

Reagents and Conditions: (i) R$^1$NH$_2$, heat, (ii) NIS, (iii)

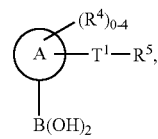

Pd(0), K$_2$CO$_3$.

Scheme 1 above shows a general synthetic route that is used for preparing the compounds I of this invention where R$^1$ and R$^2$ are as described herein. Compounds of formula I can be prepared from intermediates 1 (prepared as described in C. Thibault et al Org. Lett. 2003, 5, 5023-5026). The formation of derivatives 2 is achieved by treating the intermediate 1 with a corresponding amine. The reaction is amenable to a variety of substituted amines R$^1$—NH2. Iodination of 2 using NIS leads to a formation of 3 which can be reacted with a boronic acid derivative to give compounds of formula I, using Suzuki coupling methods that are well known in the art. The reaction is amenable to a variety of aryl boronic acid derivatives

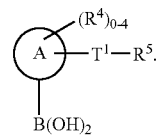

Scheme 2

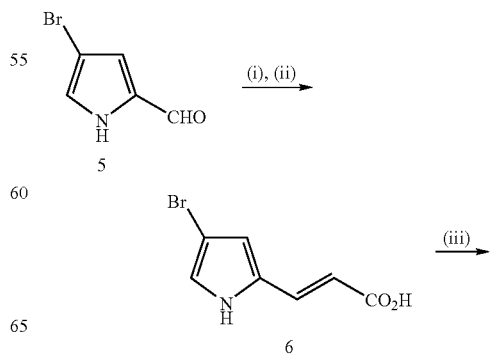

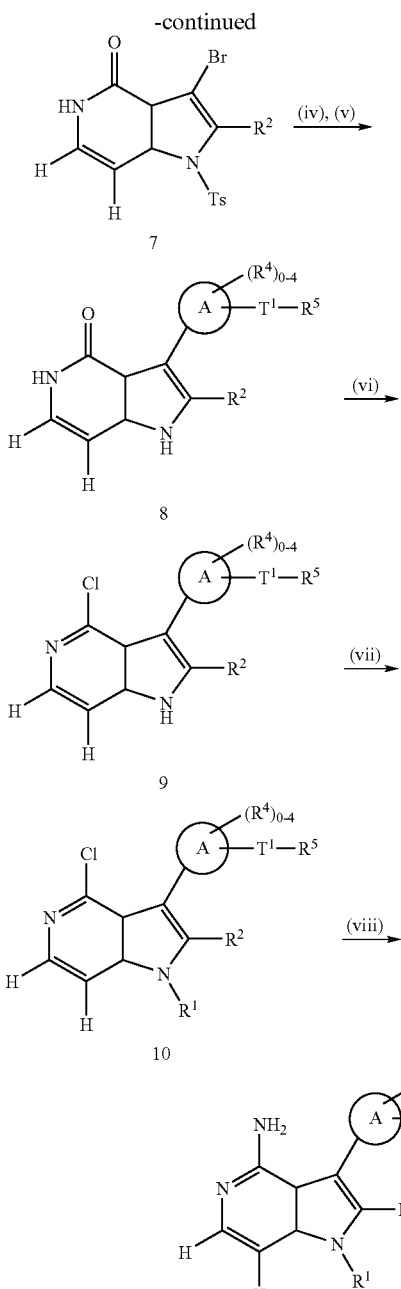

Reagents and Conditions: (i) Malonic Acid, Piperidine, (ii) 2 eq. NaH then TsCl, (iii) ClCO$_2$Et, NaN$_3$, (iv)

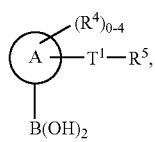

Pd(0), K$_2$CO$_3$, (v) NaOH, (vi) POCl$_3$, (vii) NaH then R$^1$X, (viii) NH$_3$ Scheme 2 above shows a general synthetic route that is used for preparing the compounds I of this invention where R$^1$ and R$^2$ are as described herein. Compounds of formula I can be prepared from intermediates 5 (prepared as described in D. Monti et al Gazz. Chim. Ital. 1990, 120, 771). The formation of derivatives 6 is achieved by treating the intermediate 5 with malonic acid in the presence of piperidine. Compound 6 is then transformed in the corresponding acylazide and is heated in a Curtius rearrangement reaction. Subsequent bromination and protection of the nitrogen as a tosylated derivative yielded compound 7. Compound 7 can be reacted with a boronic acid derivative using Suzuki coupling methods that are well known in the art. The reaction is amenable to a variety of aryl boronic acid derivatives. Compound 8 is deprotected and treated with POCl$_3$ to yield chloro derivative 9, according to steps (vi). Derivative 9 may be reacted with a variety of R$_1$X derivatives (wherein X is a halogen) to produce compound 10. Finally, treating compound 10 with ammonia forms compounds of formula I.

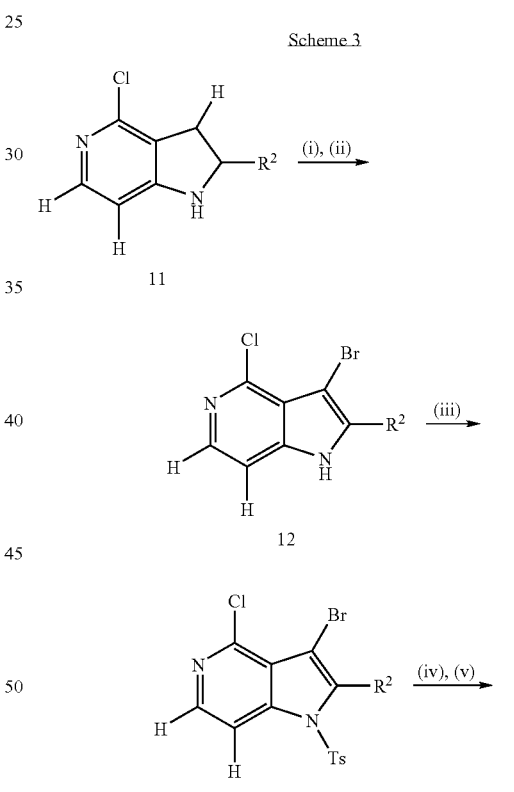

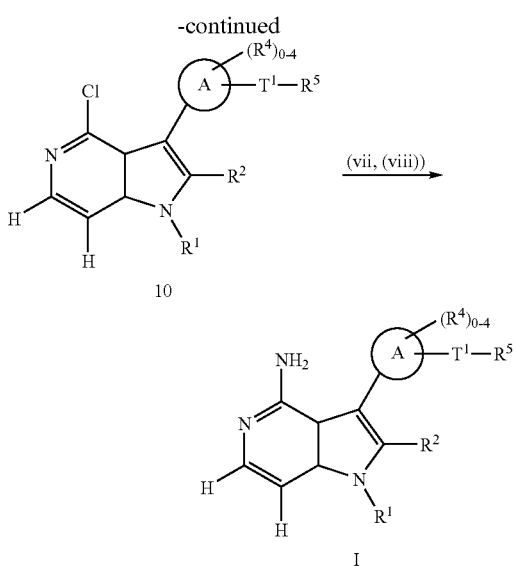

Reagents and Conditions: (i) MnO$_2$/THF (ii) NBS, CH$_2$Cl$_2$, (iii) p-TsCl, K$_2$CO$_3$, DMF (iv)

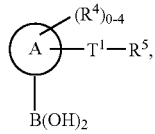

aq. K$_2$CO$_3$, Pd(PPh$_3$)$_4$, (v) aq. NaOH, MeOH (vi) NaH then R$^1$X, DMF (vii) Ph$_2$C=NH, NaOtBu, Pd$_2$(dba)$_3$, BINAP (viii) NH$_2$OH.HCl.

Scheme 3 above shows a general synthetic route that is used for preparing the compounds I of this invention where R$^1$ and

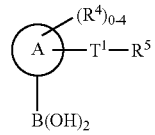

are as described herein. Compounds of formula I can be prepared from intermediates 11. The formation of derivative 12 is achieved by oxidizing the intermediate 11 with MnO$_2$ followed by bromination using NBS. Compound 12 is then transformed in the corresponding tosylate derivative 13. Compound 13 can be reacted with a boronic acid derivative using Suzuki coupling methods that are well known in the art. The reaction is amenable to a variety of aryl boronic acid derivatives. Compound 13 is subsequently deprotected to yield derivative 9. Derivative 9 may be reacted, as described in scheme 2, with a variety of R$_1$X derivatives (wherein X is halo) to produce compound 10. Finally, treating compound 10 with ammonia forms compounds of formula I.

The present invention provides compounds and compositions that are useful as inhibitors of protein kinases. In some embodiments, protein kinases are Src-family kinases. In some embodiments, Lck.

As inhibitors of protein kinases, the compounds and compositions of this invention are particularly useful for treating or lessening the severity of a disease, condition, or disorder where a protein kinase is implicated in the disease, condition, or disorder. In one aspect, the present invention provides a method for treating or lessening the severity of a disease, condition, or disorder where a protein kinase is implicated in the disease state. In another aspect, the present invention provides a method for treating or lessening the severity of a disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor.

In some embodiments, said protein kinase inhibitor is an Src-family kinase inhibitor. In some embodiment, said protein kinase inhibitor is a Lck kinase inhibitor.

As inhibitors of protein kinases, the compounds and compositions of this invention are also useful in biological samples. One aspect of the invention relates to inhibiting protein kinase activity in a biological sample, which method comprises contacting said biological sample with a compound of formula I or a composition comprising said compound. The term "biological sample", as used herein, means a sample that is not in vivo, such as an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands.

Another aspect of this invention provides compounds that are useful for the treatment of diseases, disorders, and conditions including, but not limited to, autoimmune diseases, inflammatory diseases, proliferative and hyperproliferative diseases, immunologically-mediated diseases, bone diseases, metabolic diseases, cardiovascular diseases, hormone related diseases, allergies, asthma, and Alzheimer's disease.

For example, the present invention provides compounds that are useful for treating diseases of the respiratory tract including, without limitation, reversible obstructive airways diseases including asthma, such as bronchial, allergic, intrinsic, extrinsic and dust asthma, particularly chronic or inveterate asthma (e.g., late asthma airways hyper-responsiveness) and bronchitis. Additional diseases include, without limitation, those conditions characterised by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia.

Another aspect of this invention provides compounds that are useful for treating diseases of the bone and joints including, without limitation, (pannus formation in) rheumatoid arthritis, seronegative spondyloarthropathis (including ankylosing spondylitis, psoriatic arthritis and Reiter's disease), Behcet's disease, Sjogren's syndrome, and systemic sclerosis.

Another aspect of this invention provides compounds that are useful for treating diseases and disorders of other tissues and systemic disease, including, without limitation, multiple sclerosis, atherosclerosis, acquired immunodeficiency syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas), artherosclerosis, and systemic lupus erythematosus.

Another aspect of this invention provides compounds that are useful for allograft rejection, including, without limitation, acute and chronic allograft rejection following for example transplantation of kidney, heart, liver, lung, bone marrow, skin and cornea; and chronic graft versus host disease.

Another aspect of this invention provides a method for the treatment or lessening the severity of a disease selected from an autoimmune disease, an inflammatory disease, a proliferative or hyperproliferative disease, such as cancer, an immunologically-mediated disease, a bone disease, a metabolic disease, a neurological or neurodegenerative disease, a cardiovascular disease, allergies, asthma, Alzheimer's disease, or a hormone related disease, comprising administering an effective amount of a compound, or a pharmaceutically acceptable composition comprising a compound, to a subject in need thereof.

The term "cancer" includes, but is not limited to the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon, adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; and leukemia.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

In some embodiments, said disease is selected from a proliferative disorder, a neurodegenerative disorder, an autoimmune disorder, and inflammatory disorder, and an immunologically-mediated disorder. In some embodiments, said disease is selected from hypercalcemia, restenosis, osteoporosis, osteoarthritis, symptomatic treatment of bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obstructive pulmonary disorder, contact dermatitis, cancer, Paget's disease, asthma, ischemic or reperfusion injury, allergic disease, atopic dermatitis, and allergic rhinitis. Diseases that are affected by Src activity, in particular, include hypercalcemia, osteoporosis, osteoarthritis, cancer, symptomatic treatment of bone metastasis, and Paget's disease. In other embodiments, said disease is selected from hypercalcemia, osteopetrosis, osteoarthritis, or symptomatic treatment of bone metastasis.

In yet other embodiments, said disease is a protein-kinase mediated condition. In some embodiments, said disease is an Src-mediated or Lck-mediated disease.

The term "protein kinase-mediated condition", as used herein, means any disease or other deleterious condition in which a protein kinase plays a role. Such conditions include, without limitation, autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease.

The term "Src-mediated or Lck-mediated disease", as used herein means any disease or other deleterious condition in which Src or Lck is known to play a role. Accordingly, these compounds are useful for treating diseases or conditions that are affected by the activity of one or more Src-family kinases. Such diseases or conditions include hypercalcemia, restenosis, osteoporosis, osteoarthritis, symptomatic treatment of bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obstructive pulmonary disorder, contact dermatitis, cancer, Paget's disease, asthma, ischemic or reperfusion injury, allergic disease, atopic dermatitis, and allergic rhinitis. Diseases that are affected by Src activity, in particular, include hypercalcemia, osteoporosis, osteoarthritis, cancer, symptomatic treatment of bone metastasis, and Paget's disease. Diseases that are affected by Lck activity, in particular, include autoimmune diseases, allergies, rheumatoid arthritis, and leukemia.

In another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

As described herein, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are another embodiment of the present invention. In some embodiments, said protein kinase-mediated condition is an Src-mediated or Lck-mediated condition.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled.

Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of this invention can also exist as pharmaceutically acceptable derivatives.

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable ester, salt of an ester or other derivative of a compound of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a protein kinase-mediated condition (in some embodiments, an Src or Lck-mediated condition) comprising the step of administering to a patient one of the above-described pharmaceutical compositions. The term "patient", as used herein, means an animal, preferably a human.

In some embodiments, said method is used to treat or prevent a condition selected from (Lck diseases) hypercalcemia, osteopetrosis, osteoarthritis, symptomatic treatment of bone metastasis, or any specific disease described above.

Another aspect of the invention relates to inhibiting protein kinase activity in a patient, which method comprises administering to the patient a compound of formula I, or a composition comprising said compound.

Depending upon the particular protein kinase-mediated conditions to be treated or prevented, additional drugs, which are normally administered to treat or prevent that condition, may be administered together with the inhibitors of this invention. For example, chemotherapeutic agents or other anti-proliferative agents may be combined with the protein kinase inhibitors of this invention to treat proliferative diseases.

Those additional agents may be administered separately, as part of a multiple dosage regimen, from the protein kinase inhibitor-containing compound or composition. Alternatively, those agents may be part of a single dosage form, mixed together with the protein kinase inhibitor in a single composition.

The compounds of this invention may be prepared in general by methods known to those skilled in the art. Those compounds may be analyzed by known methods, including but not limited to LCMS (liquid chromatography mass spectrometry) and NMR (nuclear magnetic resonance). Compounds of this invention may be also tested according to these examples. It should be understood that the specific conditions shown below are only examples, and are not meant to limit the scope of the conditions that can be used for making, analyzing, or testing the compounds of this invention. Instead, this invention also includes conditions known to those skilled in that art for making, analyzing, and testing the compounds of this invention.

EXAMPLES

As used herein, the term "Rt(min)" refers to the HPLC retention time, in minutes, associated with the compound. Unless otherwise indicated, the HPLC method utilized to obtain the reported retention time is as follows:
Column: ACE C8 column, 4.6×150 mm
Gradient: 0-100% acetonitrile+methanol 60:40 (20 mM Tris phosphate)
Flow rate: 1.5 mL/minute
Detection: 225 nm.

Mass spec. samples are analyzed on a MicroMass Quattro Micro mass spectrometer operated in single MS mode with electrospray ionization. Samples are introduced into the mass spectrometer using chromatography.

$^1$H-NMR spectra are recorded at 400 MHz using a Bruker DPX 400 instrument. The following compounds of formula I were prepared and analyzed as follows.

Intermediate 1

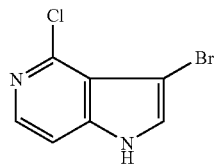

3-Bromo-4-chloro-1H-pyrrolo[3,2-c]pyridine

To a solution of the amine (2.18 g, 14.2 mmol) in THF (60 mL) was added MnO$_2$ (7 g, 80.5 mmol) and the mixture was heated to reflux. After 5 h, a further portion of MnO$_2$ (3 g, 34.5 mmol) was added and stirring continued overnight. The reaction was filtered through Celite and concentrated to give a white solid (1.95 g, 91%).

The indole (1.48 g, 9.72 mmol) was dissolved in CH2Cl2 (50 mL) and cooled to 0° C. under nitrogen. N-Bromosuccinimide (1.82 g, 10.2 mmol) was added and after 30 min the ice-bath was removed and stirring continued for a further 30 min. The desired bromide (1.53 g, 68%) was filtered off and dried on high vacuum. MS (ES+) m/e=231. 1H NMR (DMSO) 7.48 (1H, d), 7.80 (1H, s), 8.00 (1H, d).

Intermediate 2

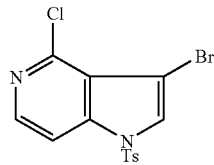

3-Bromo-4-chloro-1-tosyl-1H-pyrrolo[3,2-c]pyridine

Added p-TsCl (1.33 g, 6.95 mmol) to potassium carbonate (3.66 g, 26.5 mmol) and the indole (1.53 g, 6.62 mmol) in N,N-DMF (35 mL) at rt. After 3 h, added a further portion of p-TsCl (1.33 g, 6.95 mmol). After stirring for a further 30 min the reaction was concentrated in vacuo and then water and EtOAc (containing a small amount of THF and MeOH) were added. Re-extracted with EtOAc and then the organics were washed with brine. On concentration of the organics, the product (2.00 g, 78%) precipitated as a white solid and was collected on a frit. MS (ES+) m/e=387. 1H NMR (DMSO) 2.37 (3H, s), 7.47 (2H, d), 8.03 (2H, d), 8.04 (1H, d), 8.30 (1H, d), 8.40 (1H, s).

Intermediate 3

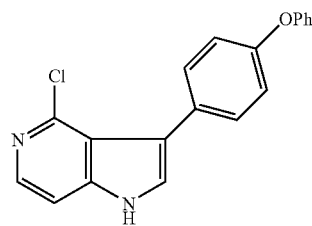

4-Chloro-3-(4-phenoxyphenyl)-1H-pyrrolo[3,2-c]pyridine

A mixture of the bromide (554 mg, 1.44 mmol), Pd(PPh$_3$)4 (164 mg, 0.14 mmol), 2M K$_2$CO$_3$ (2.14 mL, 4.28 mmol), 4-phenoxyphenylboronic acid (399 mg, 1.86 mmol) in toluene (25 mL) and ethanol (5 mL) was microwaved at 140° C. for 1 h. Then the reaction mixture was extracted into EtOAc and dried (MgSO$_4$) and filtered and concentrated. The residue was passed through a silica plug (eluting with 1/1 PE/EtOAc) and then concentrated. To this material was added MeOH (10 mL) and 2M NaOH (6 mL) and the reaction flask immersed in an oil bath at 70° C. After 40 min CH$_2$Cl$_2$ and sat. aq. NaHCO$_3$ were added. The aqueous layer was re-extracted and then the combined organics were dried (MgSO$_4$), filtered and concentrated. Purification by column chromatography (eluting with EtOAc) gave the title compound (96 mg, 21%). MS (ES+) m/e=321.

Intermediate 4

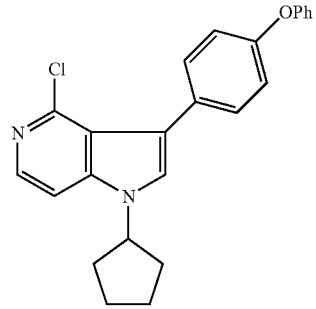

4-Chloro-1-cyclopentyl-3-(4-phenoxyphenyl)-1H-pyrrolo[3,2-c]pyridine

NaH (60% dispersion in mineral oil; 140 mg, 3.50 mmol) was added to the indole (56 mg, 0.18 mmol) at rt in anhydrous DMF (1.5 mL). After 10 min, cyclopentylbromide (264 mg, 0.18 mmol) was added and the reaction mixture was stirred overnight. Then carefully added water then EtOAc and extracted. The organic layer was washed with brine and then dried (MgSO4), filtered and concentrated. Purification by column chromatography (eluting with EtOAc/PE, 1/1) gave the title compound (45 mg, 76%). MS (ES+) m/e=389.

Example 1

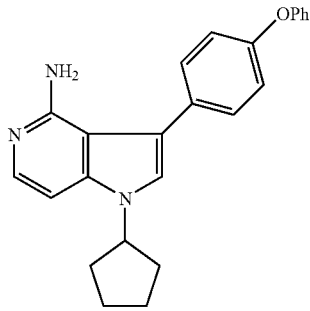

1-Cyclopentyl-3-(4-phenoxyphenyl)-1H-pyrrolo[3,2-c]pyridin-4-amine (I-1)

To a mixture of BINAP (12.5 mg, 0.02 mmol), sodium tert-butoxide (36 mg, 0.38 mmol), benzophenone imine (49 mg, 0.27 mmol) and starting chloride (52 mg, 0.13 mmol) in anhydrous toluene (5 mL) was added tris(dibenzylideneacetone)dipalladium(0) (6 mg, 0.007 mmol) under nitrogen and the mixture heated to 110° C. for 90 min. The reaction mixture was cooled and then passed through Celite with the aid of EtOAc and then concentrated. The residue was dissolved in methanol (8 mL) and then hydroxylamine hydrochloride (183 mg, 2.63 mmol) in water (2 mL) was added followed by sodium bicarbonate (221 mg, 2.63 mmol) and the mixture stirred for 3 hours. The organics were removed in vacuo and then EtOAc and brine were added. The aqueous layer was re-extracted with EtOAc and the combined organics were dried (MgSO4), filtered and concentrated. Purification by preparatory HPLC gave the aromatic amine (15 mg, 27%) as a white solid. MS (ES+) m/e=370. 1H NMR (CDCl3) 1.72-2.09 (6H, m), 2.20-2.32 (2H, m), 4.78 (1H, quin), 5.42 (2H, br s), 6.81 (1H, d), 7.07-7.12 (5H, m), 7.17 (1H, t), 7.41 (2H, t), 7.44 (2H, d), 7.72 (1H, d). HPLC rt (min): 12.1

Example 2

The compounds are evaluated as inhibitors of human Src kinase using a spectrophotometric assay.

Src Inhibition Assay: Spectrophotometric Assay

An assay buffer solution was prepared which consisted of 25 mM HEPES (pH 7.5), 10 mM $MgCl_2$, 250 μM NADH, 3 mM phosphoenolpyruvate, 60 μg/mL pyruvate kinase, 21 μg/mL lactate dehydrogenase, 113 μM ATP and 28 nM Src. To 60 μL of this solution, in a 96 well plate, was added 2 μL of test compound stock solution in DMSO and the mixture allowed to equilibrate for 10 mins at 30° C. The enzyme reaction was initiated by the addition of 5 μL 10 mg/mL poly Glu, Tyr (4:1) prepared in 25 mM HEPES (pH 7.5). Final assay concentrations of Src and ATP were 25 nM and 100 μM respectively. Initial rate data was determined from the rate of change of absorbance at 340 nM (corresponding to stoichiometric consumption of NADH) using a Molecular Devices Spectramax plate reader (Sunnyvale, Calif.) over 10 mins at 30° C. For each Ki determination 8 data points covering the test compound concentration range of 0-7.5 μM were obtained in duplicate. Ki values were calculated from initial rate data by non-linear regression using the Prism software package (Prism 4.0a, Graphpad Software, San Diego, Calif.).

Compound I-1 was found to inhibit Src at Ki<1 uM.

Example 3

The compounds are evaluated as inhibitors of human Lck kinase using a spectrophotometric assay.

Lck Inhibition Assay: Spectrophotometric Assay

An assay buffer solution was prepared which consisted of 25 mM HEPES (pH 7.5), 10 mM $MgCl_2$, 250 μM NADH, 3 mM phosphoenolpyruvate, 43 μg/mL pyruvate kinase, 14 μg/mL lactate dehydrogenase, 560 μM ATP and 67 nM Lck. To 60 μL of this solution, in a 96 well plate, was added 2 μL of test compound stock solution in DMSO and the mixture allowed to equilibrate for 10 minutes at 30° C. The enzyme reaction was initiated by the addition of 5 μL 15 mg/mL poly Glu, Tyr (4:1) prepared in 25 mM HEPES (pH 7.5). Final assay concentrations of Lck and ATP are 60 nM and 500 μM respectively. Initial rate data was determined from the rate of change of absorbance at 340 nM (corresponding to stoichiometric consumption of NADH) using a Molecular Devices Spectramax plate reader (Sunnyvale, Calif.) over 10 min at 30° C. For each Ki determination 8 data points covering the test compound compound concentration range of 0-7.5 μM are obtained in duplicate. Ki values are calculated from initial rate data by non-linear regression using the Prism software package (Prism 4.0a, Graphpad Software, San Diego, Calif.).

Compound I-1 was found to inhibit Lck at Ki<1 uM.

While we have described a number of embodiments of this invention, it is apparent that our basic examples may be altered to provide other embodiments that utilize or encompass the compounds, methods, and processes of this invention. Therefore, it will be appreciated that the scope of this invention is to be defined by the appended claims.

We claim:

1. A compound selected from the following:

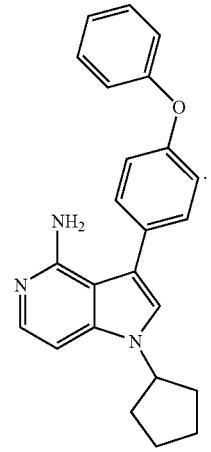

2. A compound of formula I:

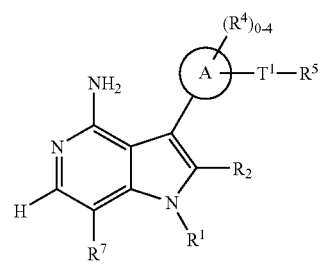

wherein
R$^1$ is C$_{1-6}$haloalkyl, Q, or -Z-Q;
R$^2$ is H, halo, CN, NO$_2$, C$_{1-4}$haloaliphatic, C$_{3-6}$cycloaliphatic, or C$_{1-6}$aliphatic;

Ring A is an 8-12 membered saturated, partially unsaturated, or fully unsaturated bicyclic ring having 0-5 heteroatoms independently selected from O, N, and S;

$R^4$ is H, $C_{1-6}$aliphatic, $C_{3-6}$cycloaliphatic, or $-(Y)_n-V^1$; wherein n is 0 or 1;

Y is unsubstituted $C_{1-6}$aliphatic optionally replaced with 0-3 occurrences of $-NR-$, $-O-$, $-S-$, $-C(O)-$, $-SO-$, or $-SO_2-$;

$V^1$ is $C_{3-6}$cycloaliphatic, halo($C_{1-4}$ aliphatic), 3-6 membered heterocyclyl, halo, $NO_2$, CN, OH, OR", SH, SR", $NH_2$, NHR", $N(R")_2$, COH, COR", $CO_2H$, $CO_2R"$, $CONH_2$, CONHR", $CONR"_2$, OCOR", $OCONH_2$, OCONHR", $OCON(R")_2$, NHCOR", NR"COR", $NHCO_2R"$, $NR"CO_2R"$, $NHCO_2H$, $NR"CO_2H$, $NHCONH_2$, NHCONHR", $NHCON(R")_2$, $SO_2NH_2$, $SO_2NHR"$, $SO_2N(R")_2$, $NHSO_2R"$, or $NR"SO_2R"$;

R" is unsubstituted $C_{1-4}$ aliphatic;

$T^1$ is $C_{1-6}$aliphatic optionally replaced with 0-3 occurrences of $-NR-$, $-O-$, $-S-$, $-C(O)-$, $-C(=NR)-$, $-C(=NOR)-$, $-SO-$, or $-SO_2-$;

each $T^1$ is optionally substituted with 0-2 $J^T$;

$R^5$ is H; $C_{1-6}$aliphatic optionally replaced with 0-2 occurrences of O, N, and S; 3-8-membered saturated, partially unsaturated, or fully unsaturated monocyclic ring having 0-3 heteroatoms independently selected from O, N, and S; or an 8-12 membered saturated, partially unsaturated, or fully unsaturated bicyclic ring having 0-5 heteroatoms independently selected from O, N, and S;

each $R^5$ is optionally substituted with 0-5 $J^5$;

$R^7$ is H or halo;

Z is $C_{1-6}$aliphatic optionally replaced with 0-3 occurrences of $-NR-$, $-O-$, $-S-$, $-C(O)-$, $-C(S)-$, $-C(=NR)-$, $-C(=NOR)-$, $-SO-$, or $-SO_2-$;

each Z is optionally substituted with 0-2 $J^Z$;

Q is H; $C_{1-6}$ aliphatic; a 3-8-membered saturated, partially unsaturated, or fully unsaturated monocyclic ring having 0-3 heteroatoms independently selected from O, N, and S; or an 8-12 membered saturated, partially unsaturated, or fully unsaturated bicyclic ring having 0-5 heteroatoms independently selected from O, N, and S;

each Q is optionally substituted with 0-5 $J^Q$;

each $J^Z$ is independently H, halo, $C_{1-6}$ aliphatic, $C_{3-6}$cycloaliphatic, $NO_2$, CN, $-NH_2$, $-NH(C_{1-4}$ aliphatic), $-N(C_{1-4}$ aliphatic$)_2$, $-OH$, $-O(C_{1-4}$ aliphatic), $-CO_2H$, $-CO_2(C_{1-4}$ aliphatic), $-O(haloC_{1-4}$ aliphatic), or halo($C_{1-4}$ aliphatic);

$J^5$ is M or $-Y-M$;

each Y is independently an unsubstituted $C_{1-6}$aliphatic optionally replaced with 0-3 occurrences of $-NR-$, $-O-$, $-S-$, $-C(O)-$, $-SO-$, or $-SO_2-$;

each M is independently H, $C_{1-6}$ aliphatic, $C_{3-8}$cycloaliphatic, halo($C_{1-4}$ aliphatic), $-O(haloC_{1-4}$ aliphatic), 3-8 membered heterocyclyl, halo, $NO_2$, CN, OH, OR', SH, SR', $NH_2$, NHR', $N(R')_2$, COH, COR', $CO_2H$, $CO_2R'$, $CONH_2$, CONHR', $CONR'_2$, OCOR', $OCONH_2$, OCONHR', $OCON(R')_2$, NHCOR', NR'COR', $NHCO_2R'$, $NR'CO_2R'$, $NHCO_2H$, $NR'CO_2H$, $NHCONH_2$, NHCONHR', $NHCON(R')_2$, $SO_2NH_2$, $SO_2NHR'$, $SO_2N(R')_2$, $NHSO_2R'$, $NR'SO_2R'$, POR', $PO_2R'$, $PO(R')_2$, or $PO(OR')_2$;

$J^Q$ is $M^1$ or $-Y^1-M^1$;

each $Y^1$ is independently an unsubstituted $C_{1-6}$aliphatic optionally replaced with 0-3 occurrences of $-NR-$, $-O-$, $-S-$, $-C(O)-$, $-SO-$, or $-SO_2-$;

each $M^1$ is independently H, $C_{1-6}$ aliphatic, $C_{3-8}$cycloaliphatic, halo($C_{1-4}$ aliphatic), $-O(haloC_{1-4}$ aliphatic), 3-8 membered heterocyclyl, 5-6 membered heteroaryl, phenyl, halo, $NO_2$, CN, OH, OR', SH, SR', $NH_2$, NHR', $N(R')_2$, COH, COR', $CO_2H$, $CO_2R'$, $CONH_2$, CONHR', $CONR'_2$, OCOR', $OCONH_2$, OCONHR', $OCON(R')_2$, NHCOR', NR'COR', $NHCO_2R'$, $NR'CO_2R'$, $NHCO_2H$, $NR'CO_2H$, $NHCONH_2$, NHCONHR', $NHCON(R')_2$, $SO_2NH_2$, $SO_2NHR'$, $SO_2N(R')_2$, $NHSO_2R'$, $NR'SO_2R'$, POR', $PO_2R'$, $PO(R')_2$, or $PO(OR')_2$;

each M and $M^1$ is independently and optionally substituted with 0-5 $J^M$;

R is H or unsubstituted $C_{1-6}$aliphatic;

R' is unsubstituted $C_{1-6}$aliphatic; or two R' groups, together with the atom to which they are bound, form an unsubstituted 3-8 membered nonaromatic monocyclic ring having 0-1 heteroatoms independently selected from O, N, and S;

each $J^T$ and $J^M$ is independently H, halo, $C_{1-6}$ aliphatic, $C_{3-6}$cycloaliphatic, $NO_2$, CN, $-NH_2$, $-NH(C_{1-4}$ aliphatic), $-N(C_{1-4}$ aliphatic$)_2$, $-OH$, $-O(C_{1-4}$ aliphatic), COH, $-CO(C_{1-4}$ aliphatic), $CONH_2$, CONH($C_{1-4}$ aliphatic), $CON(C_{1-4}$ aliphatic$)_2$, $-CO_2H$, $-CO_2(C_{1-4}$ aliphatic), $-O(haloC_{1-4}$ aliphatic), or halo($C_{1-4}$ aliphatic).

3. The compound of claim 2, wherein $R_2$ is H.

4. The compound of claim 3, wherein $R_1$ is Q.

5. The compound of claim 4, wherein Q is a 3-8-membered saturated, partially unsaturated, or fully unsaturated monocyclic ring having 0-3 heteroatoms independently selected from O, N, and S.

6. The compound of claim 5, wherein Q is a 3-8-membered saturated monocyclic ring having 0-3 heteroatoms independently selected from O, N, and S.

7. The compound of claim 6, wherein Q is a 3-8-membered saturated monocyclic ring having 0 heteroatoms.

8. The compound of claim 7, wherein Q is cyclohexyl or cyclopentyl.

9. The compound of claim 8, wherein $J^Q$ is a 3-8 membered heterocyclyl.

10. The compound of claim 9, wherein $J^Q$ is a 6-membered heterocyclyl containing 1-2 nitrogen atoms.

11. The compound of claims 2, wherein T is $-C(O)NR-$ or $-NRC(O)-$.

12. The compound of claim 11, wherein R is H.

13. The compound of claim 2, wherein $R^5$ is a 3-8-membered saturated, partially unsaturated, or fully unsaturated monocyclic ring having 0-3 heteroatoms independently selected from O, N, and S; or an 8-12 membered saturated, partially unsaturated, or fully unsaturated bicyclic ring having 0-5 heteroatoms independently selected from O, N, and S.

14. The compound of claim 13, wherein $R^5$ is fully unsaturated.

15. The compound of claim 13, wherein $R^5$ is partially unsaturated or saturated.

16. The compound of claim 2, wherein $R^4$ is H, halo, $C_{1-6}$aliphatic, $C_{3-6}$cycloaliphatic, $NO_2$, CN, $-NH_2$, $-NH(C_{1-4}$ aliphatic), $-N(C_{1-4}$ aliphatic$)_2$, $-OH$, $-O(C_{1-4}$ aliphatic), $CONH_2$, CONH($C_{1-4}$ aliphatic), $CON(C_{1-4}$ aliphatic$)_2$, COH, $-CO(C_{1-4}$ aliphatic), $-CO_2H$, $-CO_2(C_{1-4}$ aliphatic), $-O(haloC_{1-4}$ aliphatic), or halo($C_{1-4}$ aliphatic).

17. A compound of formula I:

[Structure I: pyrrolopyridine with NH₂, N, H, R⁷ on the pyridine ring; R¹, R² on pyrrole; and ring A with (R⁴)₀₋₄ and T¹—R⁵ substituent]

wherein

R¹ is $C_{1-6}$haloalkyl, Q, or -Z-Q;

R² is H, halo, CN, $NO_2$, $C_{1-4}$haloaliphatic, $C_{3-6}$cycloaliphatic, or $C_{1-6}$aliphatic;

Ring A is a 3-8-membered saturated, partially unsaturated, or fully unsaturated monocyclic ring having 0-3 heteroatoms independently selected from O, N, and S; or an 8-12 membered saturated, partially unsaturated, or fully unsaturated bicyclic ring having 0-5 heteroatoms independently selected from O, N, and S;

R⁴ is H, $C_{1-6}$aliphatic, $C_{3-6}$cycloaliphatic, or —(Y)$_n$—V¹; wherein n is 0 or 1;

Y is unsubstituted $C_{1-6}$aliphatic optionally replaced with 0-3 occurrences of —NR—, —O—, —S—, —C(O)—, —SO—, or —$SO_2$—;

V¹ is $C_{3-6}$cycloaliphatic, halo($C_{1-4}$aliphatic), 3-6 membered heterocyclyl, halo, $NO_2$, CN, OH, OR'', SH, SR'', $NH_2$, NHR'', N(R'')$_2$, COH, COR'', $CO_2H$, $CO_2R''$, $CONH_2$, CONHR'', CONR''$_2$, OCOR'', $OCONH_2$, OCONHR'', OCON(R'')$_2$, NHCOR'', NR''COR'', $NHCO_2R''$, $NR''CO_2R''$, $NHCO_2H$, $NR''CO_2H$, $NHCONH_2$, NHCONHR'', NHCON(R'')$_2$, $SO_2NH_2$, $SO_2NHR''$, $SO_2N(R'')_2$, $NHSO_2R''$, or $NR''SO_2R''$;

R'' is unsubstituted $C_{1-4}$ aliphatic;

T¹ is —C(O)NR— or —NRC(O)—

R⁵ is H; $C_{1-6}$aliphatic optionally replaced with 0-2 occurrences of O, N, and S; 3-8-membered saturated, partially unsaturated, or fully unsaturated monocyclic ring having 0-3 heteroatoms independently selected from O, N, and S; or an 8-12 membered saturated, partially unsaturated, or fully unsaturated bicyclic ring having 0-5 heteroatoms independently selected from O, N, and S; each R⁵ is optionally substituted with 0-5 J⁵;

R⁷ is H or halo;

Z is $C_{1-6}$aliphatic optionally replaced with 0-3 occurrences of —NR—, —O—, —S—, —C(O)—, —C(S)—, —C(=NR)—, —C(=NOR)—, —SO—, or —$SO_2$—; each Z is optionally substituted with 0-2 J$^Z$;

Q is H; $C_{1-6}$ aliphatic; a 3-8-membered saturated, partially unsaturated, or fully unsaturated monocyclic ring having 0-3 heteroatoms independently selected from O, N, and S; or an 8-12 membered saturated, partially unsaturated, or fully unsaturated bicyclic ring having 0-5 heteroatoms independently selected from O, N, and S; each Q is optionally substituted with 0-5 J$^Q$;

each J$^Z$ is independently H, halo, $C_{1-6}$ aliphatic, $C_{3-6}$cycloaliphatic, $NO_2$, CN, —$NH_2$, —NH($C_{1-4}$ aliphatic), —N($C_{1-4}$ aliphatic)$_2$, —OH, —O($C_{1-4}$ aliphatic), $CO_2H$, —$CO_2$($C_{1-4}$ aliphatic), —O(halo$C_{1-4}$ aliphatic), or halo($C_{1-4}$ aliphatic);

J⁵ is M or —Y-M;

each Y is independently an unsubstituted $C_{1-6}$aliphatic optionally replaced with 0-3 occurrences of —NR—, —O—, —S—, —C(O)—, —SO—, or —$SO_2$—;

each M is independently H, $C_{1-6}$ aliphatic, $C_{3-8}$cycloaliphatic, halo($C_{1-4}$ aliphatic), —O(halo$C_{1-4}$ aliphatic), halo, $NO_2$, CN, OH, OR'', SH, SR', $NH_2$, NHR', N(R')$_2$, COH, COR', $CO_2H$, $CO_2R'$, $CONH_2$, CONHR', CONR'$_2$, OCOR', $OCONH_2$, OCONHR', OCON(R')$_2$, NHCOR', NR'COR', $NHCO_2R'$, $NR'CO_2R'$, $NHCO_2H$, $NR'CO_2H$, $NHCONH_2$, NHCONHR', NHCON(R')$_2$, $SO_2NH_2$, $SO_2NHR'$, $SO_2N(R')_2$, $NHSO_2R'$, $NR'SO_2R'$, POR', $PO_2R'$, PO(R')$_2$, or PO(OR')$_2$;

J$^Q$ is M¹ or —Y¹-M¹;

each Y¹ is independently an unsubstituted $C_{1-6}$aliphatic optionally replaced with 0-3 occurrences of —NR—, —O—, —S—, —C(O)—, —SO—, or —$SO_2$—;

each M¹ is independently H, $C_{1-6}$ aliphatic, $C_{3-8}$cycloaliphatic, halo($C_{1-4}$ aliphatic), —O(halo$C_{1-4}$ aliphatic), 3-8 membered heterocyclyl, 5-6 membered heteroaryl, phenyl, halo, $NO_2$, CN, OH, OR', SH, SR', $NH_2$, NHR', N(R')$_2$, COH, COR', $CO_2H$, $CO_2R'$, $CONH_2$, CONHR', CONR'$_2$, OCOR', $OCONH_2$, OCONHR', OCON(R')$_2$, NHCOR', NR'COR', $NHCO_2R'$, $NR'CO_2R'$, $NHCO_2H$, $NR'CO_2H$, $NHCONH_2$, NHCONHR', NHCON(R')$_2$, $SO_2NH_2$, $SO_2NHR'$, $SO_2N(R')_2$, $NHSO_2R'$, $NR'SO_2R'$, POR', $PO_2R'$, PO(R')$_2$, or PO(OR')$_2$;

each M and M¹ is independently and optionally substituted with 0-5 J$^M$;

R is H or unsubstituted $C_{1-6}$aliphatic;

R' is unsubstituted $C_{1-6}$aliphatic; or two R' groups, together with the atom to which they are bound, form an unsubstituted 3-8 membered nonaromatic monocyclic ring having 0-1 heteroatoms independently selected from O, N, and S;

each J$^T$ and J$^M$ is independently H, halo, $C_{1-6}$ aliphatic, $C_{3-6}$cycloaliphatic, $NO_2$, CN, —$NH_2$, —NH($C_{1-4}$ aliphatic), —N($C_{1-4}$ aliphatic)$_2$, —OH, —O($C_{1-4}$ aliphatic), COH, —CO($C_{1-4}$ aliphatic), $CONH_2$, CONH($C_{1-4}$ aliphatic), CON($C_{1-4}$ aliphatic)$_2$, —$CO_2H$, —$CO_2$($C_{1-4}$ aliphatic), —O(halo$C_{1-4}$ aliphatic), or halo($C_{1-4}$ aliphatic);

provided that Ring A is not

[Structure: maleimide-type ring with Cy substituent]

wherein Cy is any cyclic moiety;

when Q is an optionally substituted 5-membered saturated ring with 1-3 heteroatoms selected from O and S; then J$^Q$ is not —(CH$_2$)$_q$-PO(OR)$_2$, wherein q is 0 or 1 and R is H or unsubstituted $C_{1-6}$aliphatic;

when R¹ and R² are both H, then ring A is not

[Structure: tetrahydropyridine ring]

18. The compound of claim 17, wherein $R^2$ is H.

19. The compound of claim 18, wherein $R^1$ is Q.

20. The compound of claim 19, wherein Q is a 3-8-membered saturated, partially unsaturated, or fully unsaturated monocyclic ring having 0-3 heteroatoms independently selected from O, N, and S.

21. The compound of claim 20, wherein Q is a 3-8-membered saturated monocyclic ring having 0-3 heteroatoms independently selected from O, N, and S.

22. The compound of claim 21, wherein Q is a 3-8-membered saturated monocyclic ring having 0 heteroatoms.

23. The compound of claim 22, wherein Q is cyclohexyl or cyclopentyl.

24. The compound of claim 23, wherein $J^Q$ is a 3-8 membered heterocyclyl.

25. The compound of claim 24, wherein $J^Q$ is a 6-membered heterocyclyl containing 1-2 nitrogen atoms.

26. The compound of claim 17, wherein R is H.

27. A composition comprising a compound of any one of claims 1 and 2-26, and a pharmaceutically acceptable carrier, adjuvant, or vehicle.

28. A method of inhibiting protein kinase activity in a biological sample comprising contacting said biological sample with:
   a) a composition of claim 27.

29. The method of claim 28, wherein said protein kinase is Lck.

30. A method of inhibiting protein kinase activity in a biological sample comprising contacting said biological sample with:
   a) a compound of any one of claims 1 and 2-26.

31. The method of claim 30, wherein said protein kinase is Lck.

32. A compound of formula I:

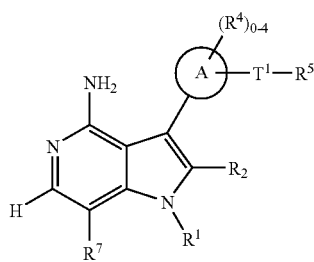

I wherein
$R^1$ is $C_{1-6}$haloalkyl, Q, or —Z—Q;
$R^2$ is H, halo, CN, $NO_2$, $C_{1-4}$haloaliphatic, $C_{3-6}$cycloaliphatic, or $C_{1-6}$aliphatic;
Ring A is a 3-8-membered saturated, partially unsaturated, or fully unsaturated monocyclic ring having 0-3 heteroatoms independently selected from O, N, and S;
$R^4$ is H, $C_{1-6}$aliphatic, $C_{3-6}$cycloaliphatic, or —(Y)$_n$-V$^1$; wherein
   n is 0 or 1;
   Y is unsubstituted $C_{1-6}$aliphatic optionally replaced with 0-3 occurrences of —NR—, —O—, —S—, —C(O)—, —SO—, or —$SO_2$—;
   $V^1$ is $C_{3-6}$cycloaliphatic, halo($C_{1-4}$ aliphatic), 3-6 membered heterocyclyl, halo, $NO_2$, CN, OH, OR", SH, SR", $NH_2$, NHR", N(R")$_2$, COH, COR", $CO_2H$, $CO_2R$", $CONH_2$, CONHR", CONR"$_2$, OCOR", $OCONH_2$, OCONHR", OCON(R")$_2$, NHCOR", NR"COR", $NHCO_2R$", $NR"CO_2R$", $NHCO_2H$, $NR"CO_2H$, $NHCONH_2$, NHCONHR", NHCON(R")$_2$, $SO_2NH_2$, $SO_2NHR$", $SO_2N(R")_2$, $NHSO_2R$", or $NR"SO_2R$";
R" is unsubstituted $C_{1-4}$ aliphatic;
$T^1$ is —O—;
$R^5$ is a 3-8-membered saturated, partially unsaturated, or fully unsaturated monocyclic ring having 0-3 heteroatoms independently selected from O, N, and S; or an 8-12 membered saturated, partially unsaturated, or fully unsaturated bicyclic ring having 0-5 heteroatoms independently selected from O, N, and S; each $R^5$ is optionally substituted with 0-5 $J^5$;
$R^7$ is H or halo;
Z is $C_{1-6}$aliphatic optionally replaced with 0-3 occurrences of —NR—, —O—, —S—, —C(O)—, —C(S)—, —C(=NR)—, —C(=NOR)—, —SO—, or —$SO_2$—; each Z is optionally substituted with 0-2 $J^Z$;
Q is H; $C_{1-6}$ aliphatic; a 3-8-membered saturated, partially unsaturated, or fully unsaturated monocyclic ring having 0-3 heteroatoms independently selected from O, N, and S; or an 8-12 membered saturated, partially unsaturated, or fully unsaturated bicyclic ring having 0-5 heteroatoms independently selected from O, N, and S; each Q is optionally substituted with 0-5 $J^Q$;
each $J^Z$ is independently H, halo, $C_{1-6}$ aliphatic, $C_{3-6}$cycloaliphatic, $NO_2$, CN, —$NH_2$, —NH($C_{1-5}$ aliphatic), —N($C_{1-4}$ aliphatic)$_2$, —OH, —O($C_{1-4}$ aliphatic), —$CO_2H$, —$CO_2$($C_{1-4}$ aliphatic), —O(halo$C_{1-4}$ aliphatic), or halo($C_{1-4}$ aliphatic);
$J^5$ is M or —Y—M;
each Y is independently an unsubstituted $C_{1-6}$aliphatic optionally replaced with 0-3 occurrences of —NR—, —O—, —S—, —C(O)—, —SO—, or —$SO_2$—;
each M is independently H, $C_{1-6}$ aliphatic, $C_{3-8}$cycloaliphatic, halo($C_{1-4}$ aliphatic), —O(halo$C_{1-4}$ aliphatic), 3-8 membered heterocyclyl, halo, $NO_2$, CN, OH, OR', SH, SR', $NH_2$, NHR', N(R')2, COH, COR', $CO_2H$, $CO_2R'$, $CONH_2$, CONHR', CONR'$_2$, OCOR', $OCONH_2$, OCONHR', OCON(R')$_2$, NHCOR', NR'COR', $NHCO_2R'$, $NR'CO_2R'$, $NHCO_2H$, $NR'CO_2H$, $NHCONH_2$, NHCONHR', NHCON(R')$_2$, $SO_2NH_2$, $SO_2NHR'$, $SO_2N(R')_2$, $NHSO_2R'$, $NR'SO_2R'$, POR', $PO_2R'$, PO(R')$_2$, or PO(OR')$_2$;
$J^Q$ is $M^1$ or —$Y^1$-$M^1$;
each $Y^1$ is independently an unsubstituted $C_{1-6}$aliphatic optionally replaced with 0-3 occurrences of —NR—, —O—, —S—, —C(O)—, —SO—, or —$SO_2$—;
each $M^1$ is independently H, $C_{1-6}$ aliphatic, $C_{3-8}$cycloaliphatic, halo($C_{1-4}$ aliphatic), —O(halo$C_{1-4}$ aliphatic), 3-8 membered heterocyclyl, 5-6 membered heteroaryl, phenyl, halo, $NO_2$, CN, OH, OR', SH, SR', $NH_2$, NHR', N(R')$_2$, COH, COR', $CO_2H$, $CO_2R'$, $CONH_2$, CONHR', CONR'$_2$, OCOR', $OCONH_2$, OCONHR', OCON(R')$_2$, NHCOR', NR'COR', $NHCO_2R'$, $NR'CO_2R'$, $NHCO_2H$, $NR'CO_2H$, $NHCONH_2$, NHCONHR', NHCON(R')$_2$, $SO_2NH_2$, $SO_2NHR'$, $SO_2N(R')_2$, $NHSO_2R'$, $NR'SO_2R'$, POR', $PO_2R'$, PO(R')$_2$, or PO(OR')$_2$;
each M and $M_1$ is independently and optionally substituted with 0-5 $J^M$;
R is H or unsubstituted $C_{1-6}$aliphatic;
R' is unsubstituted $C_{1-6}$aliphatic; or two R' groups, together with the atom to which they are bound, form an unsubstituted 3-8 membered nonaromatic monocyclic ring having 0-1 heteroatoms independently selected from O, N, and S;
each $J^T$ and $J^M$ is independently H, halo, $C_{1-6}$ aliphatic, $C_{3-6}$cycloaliphatic, $NO_2$, CN, —$NH_2$, —NH($C_{1-4}$ aliphatic), —N($C_{1-4}$ aliphatic)$_2$, —OH, —O($C_{1-4}$ aliphatic), COH, —CO($C_{1-4}$ aliphatic), $CONH_2$, CONH($C_{1-4}$ aliphatic), CON($C_{1-4}$ aliphatic)$_2$, —$CO_2H$, —$CO_2$ ($C_{1-4}$ aliphatic), —O(halo$C_{1-4}$ aliphatic), or halo($C_{1-4}$ aliphatic);
provided that
Ring A is not

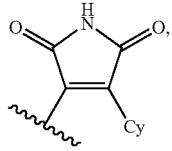

wherein Cy is any cyclic moiety;
when Q is an optionally substituted 5-membered saturated ring with 1-3 heteroatoms selected from O and S; then $J^Q$ is not —$(CH_2)_q$—PO(OR)$_2$, wherein
q is 0 or 1 and
R is H or unsubstituted $C_{1-6}$aliphatic;
when $R^1$ and $R^2$ are both H, then ring A is not

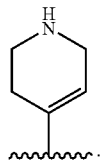

33. The compound according to claim 32, wherein Ring A is fully unsaturated.

34. The compound according to claim 32, wherein Ring A is partially unsaturated or saturated.

35. The compound according to claim 32, wherein $R^5$ is fully unsaturated.

36. The compound according to claim 35, wherein $R^4$ is H, halo, $C_{1-6}$ aliphatic, $C_{3-6}$cycloaliphatic, $NO_2$, CN, —$NH_2$, —NH($C_{1-4}$ aliphatic), —N($C_{1-4}$ aliphatic)$_2$, —OH, —O($C_{1-4}$ aliphatic), $CONH_2$, CONH($C_{1-4}$ aliphatic), CON($C_{1-4}$ aliphatic)$_2$, COH, —CO($C_{1-4}$ aliphatic), —$CO_2$H, —$CO_2$($C_{1-4}$ aliphatic), —O(halo$C_{1-4}$ aliphatic), or halo($C_{1-4}$ aliphatic).

37. The compound according to claim 32, wherein $R^5$ is partially unsaturated or saturated.

38. The compound according to claim 37, wherein $R^4$ is H, halo, $C_{1-6}$ aliphatic, $C_{3-6}$cycloaliphatic, $NO_2$, CN, —$NH_2$, —NH($C_{1-4}$ aliphatic), —N($C_{1-4}$ aliphatic)$_2$, —OH, —O($C_{1-4}$ aliphatic), $CONH_2$, CONH($C_{1-4}$ aliphatic), CON($C_{1-4}$ aliphatic)$_2$, COH, —CO($C_{1-4}$ aliphatic), —$CO_2$H, —$CO_2$($C_{1-4}$ aliphatic), —O(halo$C_{1-4}$ aliphatic), or halo($C_{1-4}$ aliphatic).

* * * * *